US006103689A

United States Patent [19]
Gilchrest et al.

[11] Patent Number: 6,103,689
[45] Date of Patent: Aug. 15, 2000

[54] METHODS OF INDUCING HAIR GROWTH AND COLORATION

[75] Inventors: Barbara A. Gilchrest, Brookline; Mina Yaar, Sharon; Mark Eller, Boston, all of Mass.

[73] Assignee: Trustees of Boston University, Boston, Mass.

[21] Appl. No.: 08/298,941

[22] Filed: Aug. 31, 1994

[51] Int. Cl.[7] .......................... A61K 38/18; A61K 38/04; A61K 38/02

[52] U.S. Cl. .................................. 514/2; 514/12; 514/880

[58] Field of Search ..................................... 514/2, 12, 880

[56] References Cited

FOREIGN PATENT DOCUMENTS

| | | |
|---|---|---|
| 0 584 452 A1 | 3/1994 | European Pat. Off. . |
| 63-183518 | 7/1988 | Japan . |
| 63-301810 | 12/1988 | Japan . |
| 92/18149 | 10/1992 | WIPO . |
| 95/21193 | 8/1995 | WIPO . |
| 96/12955 | 5/1996 | WIPO . |

OTHER PUBLICATIONS

Yaar, M., et al., "The trk Family of Receptors Mediates Nerve Growth Factor and Neurotrophin–3 Effects in Melanocytes," *J. Clin. Invest.*, 94(4):1550–1562 (1994).

Lapchak, P.A., "Nerve Growth Factor Pharmacology: Application to the Treatment of Cholinergic Neurodegeneration in Alzheimer's Disease," *Exper. Neurology*, 124:16–20 (1993).

Rudinger, In *Peptide Hormones*, ed. J. A. Parsons, University Park Press, Baltimore, pp. 1–6, 1974.

Reams, Jr., *J. Investigative Dermatol.*, vol. 49, pp. 552–558, 1967.

Rabizadeh et al., *Science*, vol. 261, pp. 345–348, 1993.

Di Marco et al., *JBC*, vol. 268, pp. 22838–22846, 1993.

Nakayama, K., et al., "Targeted Disruption of bcl–2αβ in Mice: Occurrence of Gray Hair, Polycystic Kidney Disease, and Lymphocytopenia," *Proc. Natl. Acad. Sci. USA*, 9:3700–3704 (1994).

Natataj, A., et al., "bcl–2 Oncogene Blocks Differentiation and Extends Viability but Does Not Immortalize Normal Human Keratinocytes," *Intl. J. Oncology*, 4:1211–1218 (1994).

Marchetti, D., et al., "Nerve Growth Factor Effects on Human and Mouse Melanoma Cell Invasion and Heparanase Production," *Int. J. Cancer*, 55:692–699 (1993).

Spritz, R.A., et al., "Inhibition of Proliferation of Human Melanocytes by a KIT Antisense Oligodeoxynucleotide: Implications for Human Piebaldism and Mouse Dominant White Spotting (W),", *Soc. Invest. Dermatology*, 103(2):148–150 (1994).

Zhai, S. et al., "A Role for P75 Nerve Growth Factor Receptor in Programmed Melanocyte Cell Death After Injury and With Aging," *Journal of Investigative Dermatology* 102(4):545, SID Abstract #131 (1994).

Yaar, M. et al., "Cloning and Expression of a Novel Nerve Growth Factor Related Molecule in Human Skin," *Journal of Investigative Dermatology* 100(4):548, Abstract #100 (1993).

Yaar, M. et al., "Melanocyte Function in Human Skin is Modulated by Neurotrophic Factors through TRK Receptors," *Journal of Investigative Dermatology* 100(4):511, Abstract #134 (1993).

Zhai, Sen et al., "Nerve Growth Factor (NGF) Enhances Survival of Human Melanocytes," *Journal of Investigative Dermatology* 101:434, Abstract #279 (1993).

Yaar, M. et al. "Involvement of TRK Proto–Oncogene in Physiologic Stimuli of Human Melanocytes," *Clinical Research* 40(2):531A, SID Abstracts, (1992).

Price, Vera H., "Alopecia Areata: Clinical Aspects," *Journal of Investigative Dermatology* 96(5), Supplement:68S (1991).

Yaar, Mina and Gilchrest, Barbara A, "Human Melanocyte Growth and Differentiation: A Decade of New Data," *Journal of Investigative Dermatology* 97(4):611–617 (1991).

Goldsmith, Lowell A., "Summary of Alopecia Areata Research Workshop and Future Research Directions," *Journal of Investigative Dermatology* 96(5), Supplement: 98S–100S (1991).

Friedmann, Peter S., "Clinical and Immunologic Associations of Alopecia Areata," *Seminars in Dermatology* 4(1):9–15 (1985).

Stenn, K.S. et al., "Expression of the bcl–2 Protooncogene in the Cycling Adult Mouse Hair Follicle," *Journal of Investigative Dermatology* 103(1):107–111 (1994).

Rabizadeh, Shahrooz et al., "Induction of Apoptosis by the Low–Affinity NGF Receptor," *Science* 261:345–348 (1993).

Garcia, Irene et al., "Prevention of Programmed Cell Death of Sympathetic Neurons by the bcl–2 Proto–Oncogene," *Science* 258:302–304 (1992).

Allsopp, Timothy E. et al., "The Proto–Oncogene bcl–2 Can Selectively Rescue Neurotrophic Factor–Dependent Neurons from Apoptosis," *Cell* 73:295–307 (1993).

Veis, Deborah J. et al., "Bcl–2–Deficient Mice Demonstrate Fulminant Lymphoid Apoptosis, Polycystic Kidneys, and Hypopigmented Hair," *Cell* 75:229–240 (1993).

Di Marco, Eddi et al., "Growth–regulated Synthesis and Secretion of Biologically Active Nerve Growth Factor by Human Keratinocytes," *Journal of Biological Chemistry* 266(32):21718–21722 (1991).

Yarr, Mina et al., "Evidence for Nerve Growth Factor–mediated Paracrine Effects in Human Epidermis," *Journal of Cell Biology* 115(3):821–828 (1991).

Barinaga, Marcia "Death Gives Birth to the Nervous System. But How?" *Science* 259:762–763 (1993).

(List continued on next page.)

*Primary Examiner*—Anthony C. Caputa
*Assistant Examiner*—Stephen Gucker
*Attorney, Agent, or Firm*—Hamilton, Brook, Smith & Reynolds, P.C.

[57] ABSTRACT

A method for maintaining hair growth and coloration in humans by using neurotrophin ligands to prevent p75 nerve growth factor (NGF) receptor mediated apoptosis in melanocytes and keratinocytes is described.

28 Claims, 7 Drawing Sheets

OTHER PUBLICATIONS

Hockenbery, David M. et al., "Bcl–2 Functions in an Antioxidant Pathway to Prevent Apoptosis," *Cell 75*:241–251 (1993).

Di Marco, Eddi et al., "Molecular Cloning of trkE, a Novel trk–related Putative Tyrosine Kinase Receptor Isolated from Normal Human Keratinocytes and Widely Expressed by Normal Human Tissues," *Journal of Biological Chemistry 268(32)*:24290–24295 (1993).

Peacocke, Monica et al., "Induction of nerve growth factor receptors on cultured human melanocytes," *Proc. Natl. Acad. Sci. USA 85*:5282–5286 (1988).

Barinaga, Marcia, "Cell Suicide: By Ice, Not Fire," *Science 263*:754–756 (1994).

Paus, R. et al., "Telogen skin contains an inhibitor of hair growth," *British Journal of Dermatology 122*:777–784 (1990).

Ross, Alonzo H. et al., "Characterization of nerve growth factor receptor in neural crest tumors using monoclonal antibodies," *Proc. Natl. Acad. Sci. USA 81*:6681–6685 (1984).

Halaban, R. et al., "Basic Fibroblast Growth Factor from Human Keratinocytes Is a Natural Mitogen for Melanocytes," *Journal of Cell Biology 107*:1611–1619 (1988).

Halaban, Ruth et al., "bFGF is the Putative Natural Growth Factor For Human Melanocytes," *In Vitro Cellular & Developmental Biology 23(1)*:47–52 (1987).

Ullrich, Axel et al., "Human β–nerve growth factor gene sequence highly homologous to that of mouse," *Nature 303*:821–825 (1983).

Morgenstern, Jay P. and Land, Hartmut, "Advanced mammalian gene transfer: high titre retroviral vectors with multiple drug selection markers and a complementary helper–free packaging cell line," *Nucleic Acids Research 18(12)*:3587–3596 (1990).

Johnson, Dan et al., "Expression and Structure of the Human NGF Receptor," *Cell 47*:545–554 (1986).

Heuer, Josef G. et al., "Structure and Developmental Expression of the Chicken NGF Receptor," *Developmental Biology 137*:287–304 (1990).

Large, Thomas H. et al., "Structure and Developmental Expression of the Nerve Growth Factor Receptor in the Chicken Central Nervous System," *Neuron 2*:1123–1134 (1989).

Radeke, Monte J. et al., "Gene transfer and molecular cloning of the rat nerve growth factor receptor," *Nature 325*:593–597 (1987).

Mitchell, Andrew J. and Krull, Edward A., "Alopecia areata: Pathogenesis and treatment," *Journal of the American Academy of Dermatology 11(5)I*:763–775 (1984).

Klein, Rüdiger et al., "The trk Proto–Oncogene Encodes a Receptor for Nerve Growth Factor," *Cell 65*:189–197 (1991).

Maisonpierre, Peter C. et al., "Neurotrophin–3: A Neurotrophic Factor Related to NGF and BDNF," *Science 247*:1446–1451 (1990).

Chao, Moses V. et al., "Gene Transfer and Molecular Cloning of the Human NGF Receptor," *Science 232*:518–521 (1986).

Headington, John T., "Transverse Microscopic Anatomy of the Human Scalp," *Arch. Dermatol. 120*:449–456 (1984).

Sperling, Leonard C., "Hair anatomy for the clinician," *Journal of the American Academy of Dermatology 25(1)I*:1–17 (1991).

Gilchrest, Barbara A., "Skin and Aging Processes," (Boca Raton, FL., *CRC Press, Inc.*) pp. 19–20 (1984).

Bertolino, Arthur P. et al., "Biology of Hair Follicles," In Thomas B. Fitzpatrick et al. (Ed.), *Dermatology in General Medicine,* Section 4, Chapter 19, (NY: McGraw–Hill, Inc.) pp. 289–293, Fourth Edition, (1993).

Bertolino, Arthur P. and Freedberg, Irwin M., "Hair," In Thomas B. Fitzpatrick et al. (Ed.), *Dermatology in General Medicine,* Section 10, Chapter 61, (NY: McGraw–Hill, Inc.) pp. 671–673, Fourth Edition, (1993).

FIG. IA 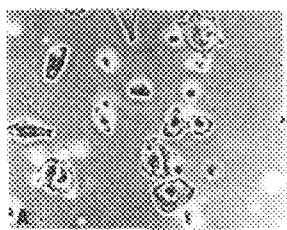
FIG. IB 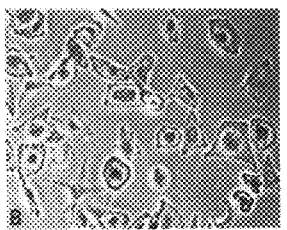
FIG. IC 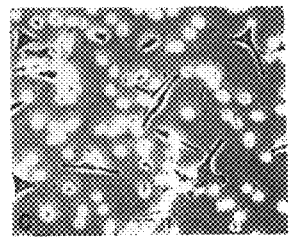
FIG. ID 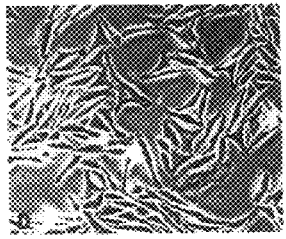
FIG. IE 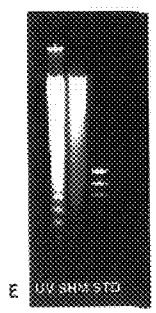
FIG. IF 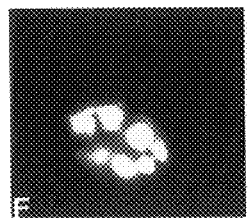
FIG. IG 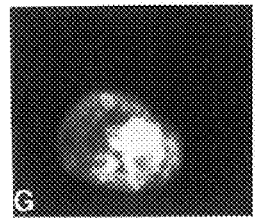
FIG. IH 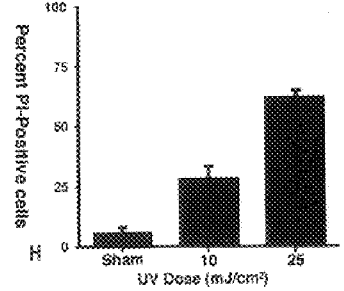

FIG. 2A
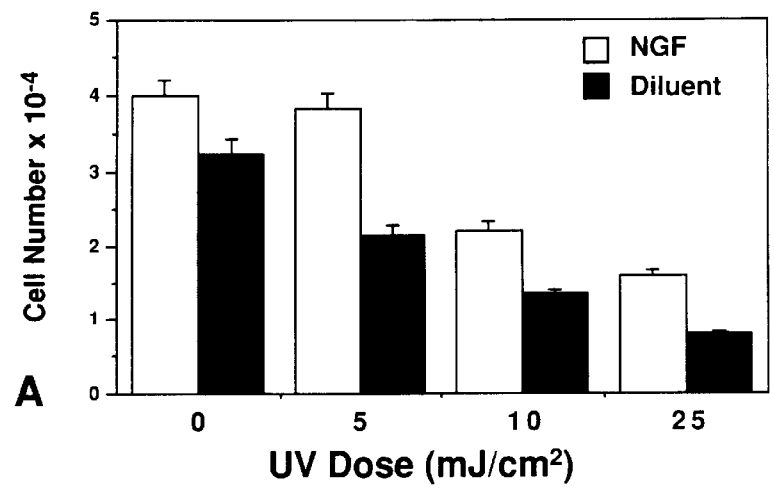
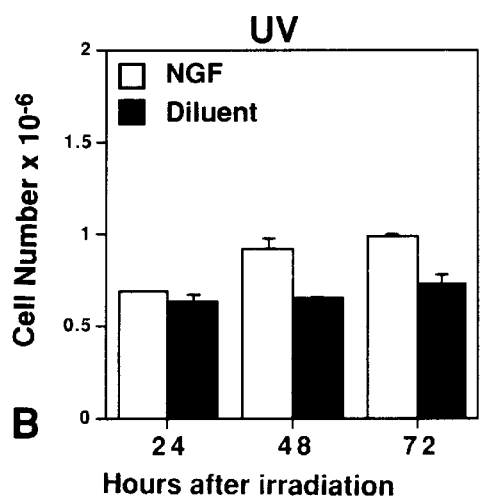
FIG. 2B
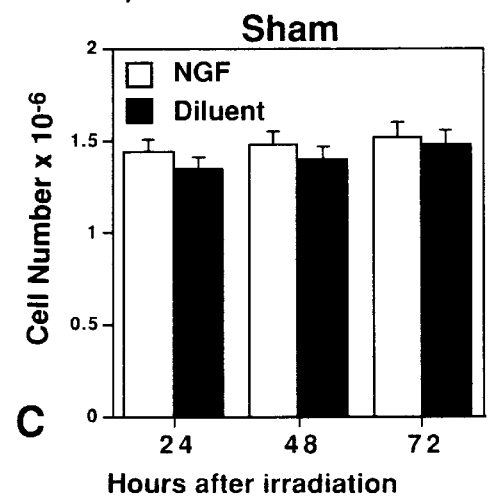
FIG. 2C
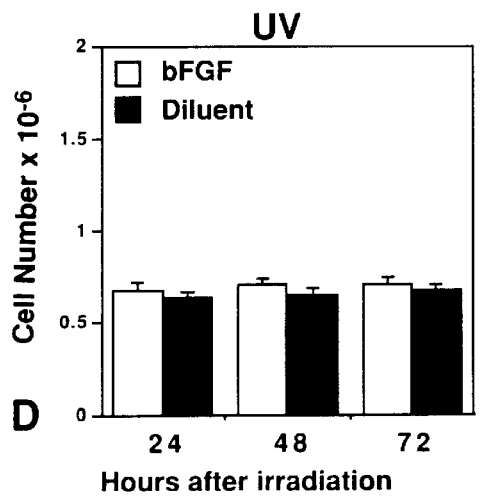
FIG. 2D
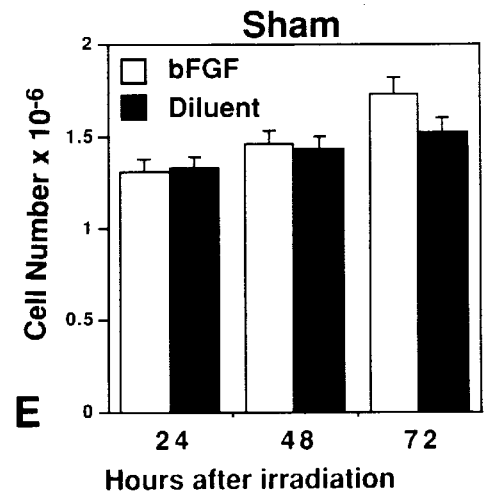
FIG. 2E FIG. 2F
FIG. 2G
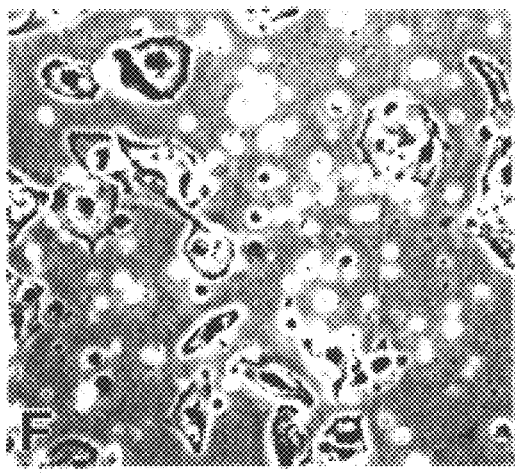
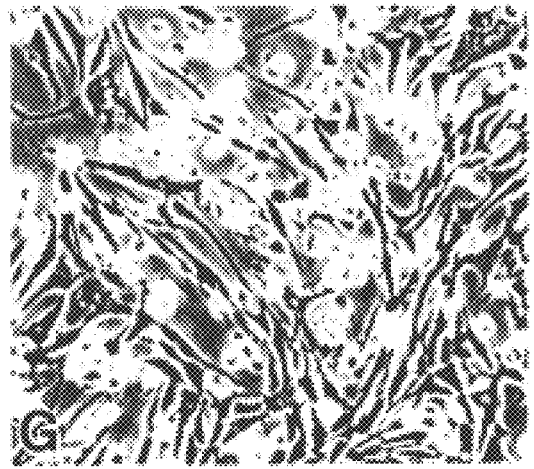
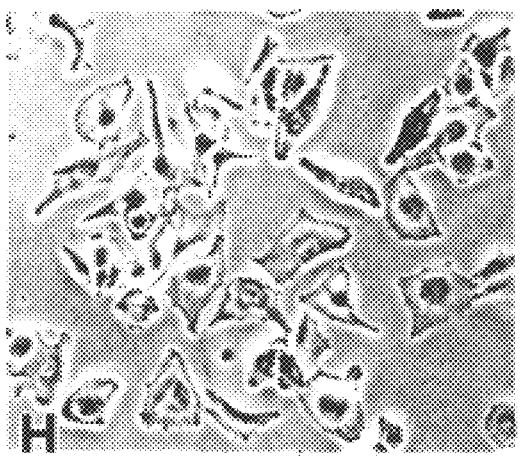
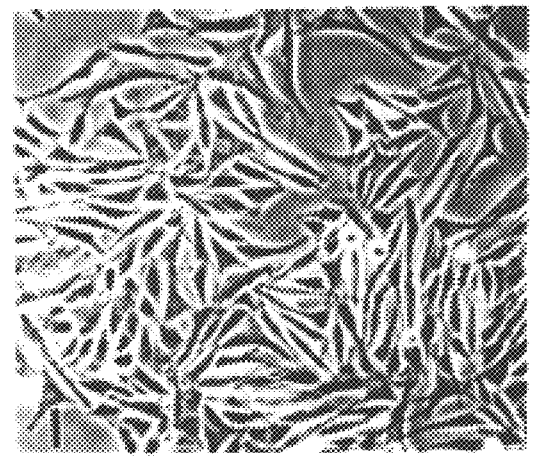
FIG. 2H
FIG. 2I

METHODS OF INDUCING HAIR GROWTH AND COLORATION

BACKGROUND OF THE INVENTION

Normal hair follicles cycle between a growth stage (anagen), a degenerative stage (catagen), and a resting stage (telogen). The scalp hairs have a relatively long life cycle: the anagen stage ranges from two to five years, the catagen stage ranges from a few days to a few weeks, and the telogen stage is approximately three months (Fitzpatrick, T. B., et al., eds., DERMATOLOGY IN GENERAL MEDICINE (Vol. I), McGraw-Hill, Inc., 1993, pp. 290–291; Sperling, L. C., *J. Amer. Acad. Dermatology* (v. 25, No. 1, Part 1), pp. 1–17 (1991)). Shorter hairs found elsewhere on the body have corresponding shorter anagen duration. The morphology of the hair and the hair follicle changes dramatically over the course of the life cycle of the hair.

During anagen, the hair follicle is highly active metabolically (Sperling, L. C., *J. Amer. Acad. Dermatology* (v. 25, No. 1, Part 1), p. 4 (1991)). The follicle comprises a follicular (dermal) papilla at the base of the follicle; epidermal matrix cells surrounding the follicular papilla and forming the base of a hair shaft; and the hair shaft that extends upwards from the papilla through the hair canal (Fitzpatrick, T. B., et al., eds., DERMATOLOGY IN GENERAL MEDICINE (Vol. I), McGraw-Hill, Inc., 1993). The matrix cells are the actively growing portion of the hair (Sperling, L. C., *J. Amer. Acad. Dermatology* (v. 25, No. 1, Part 1), p.6 (1991)). At catagen, the matrix cells retract from the papilla, and other degenerative changes occur (Sperling, L. C., *J. Amer. Acad. Dermatology* (v. 25, No. 1, Part 1), pp. 13–14 (1991)). A column of epithelial cells pushes the keratinized proximal shaft of the hair upwards (Sperling, L. C., *J. Amer. Acad. Dermatology* (v. 25, No. 1, Part 1), p. 3 (1991)), and cell death occurs within the follicle (Fitzpatrick, T. B., et al., eds., DERMATOLOGY IN GENERAL MEDICINE (Vol. I), McGraw-Hill, Inc., 1993, p. 291).

When the hair follicle reaches the telogen stage, the existing hair has a club-shaped proximal end, and a small bud (a remnant of the epithelial column that is found in catagen) at the base of the follicle (Sperling, L. C., *J. Amer. Acad. Dermatology* (v. 25, No. 1, Part 1), p. 3 (1991)). A telogen hair will not grow further (Fitzpatrick, T. B., et al., eds., DERMATOLOGY IN GENERAL MEDICINE (Vol. I), McGraw-Hill, Inc., 1993, p. 291).

The pigmentary system that colors hair involves melanocytes located in the matrix area of the follicle, above the follicular papilla (Fitzpatrick, T. B., et al., eds., DERMATOLOGY IN GENERAL MEDICINE (Vol. I), McGraw-Hill, Inc., 1993, p. 292). Melanin pigments produced by the melanocytes flow along dendritic processes (Fitzpatrick, T. B., et al., eds., DERMATOLOGY IN GENERAL MEDICINE (Vol. I), McGraw-Hill, Inc., 1993, p. 292). The dendritic processes are phagocytized by the differentiating matrix cells that become part of the hair shaft; degradation of the phagocytosed material results in release of melanin granules into the cytoplasm (Fitzpatrick, T. B., et al., eds., DERMATOLOGY IN GENERAL MEDICINE (Vol. I), McGraw-Hill, Inc., 1993, p. 671), thus pigmenting the hair.

Alterations in normal hair pigmentation or growth may be caused by age, physiologic disease conditions, or injury especially, for example, exposure to ultraviolet-irradiation. The "graying" of hair, both normal (age-associated) or abnormal, is known as canities. Graying results from a progressive decrease in pigment present in the hair shaft, caused by loss of melanocytes (Fitzpatrick, T. B., et al., eds., DERMATOLOGY IN GENERAL MEDICINE (Vol. I), McGraw-Hill, Inc., 1993, p. 671; Gilchrest, B. A., SKIN AND AGING PROCESSES, CRC Press, 1984, p. 19). A decrease in the density of hair follicles is also associated with advancing age (Gilchrest, B. A., SKIN AND AGING PROCESSES, CRC Press, 1984, p. 20).

To date, the mechanism of melanocyte and keratinocyte injury, for example, from ultraviolet exposure or the aging process, has not been determined. Thus, little is known or available regarding a mechanism to manipulate the injury process to prevent cell death and thus prevent premature baldness or graying of hair or, conversely, to promote cell death and thus, unwanted hair growth.

SUMMARY OF THE INVENTION

The present invention is based on Applicants' discovery that basal layer epidermal melanocytes and keratinocytes undergo characteristic programmed cell death in response to injury. In particular, Applicants have shown that epidermal melanocytes and keratinocytes undergo programmed cell death, or apoptosis, and that apoptosis in these cells is mediated by the p75 nerve growth factor receptor/nerve growth factor pathway (p75 NGF-R/NGF), resulting in upregulation of Bcl-2 protein. As a result of Applicants'discovery, methods are herein provided to control, or manipulate, melanocyte and keratinocyte cell death by altering the effects of apoptosis. For example, apoptosis can be inhibited using methods described herein, resulting in hair growth and coloration. Conversely, apoptosis can be promoted by methods described herein, resulting in hair loss or depigmentation.

Keratinocytes and melanocytes of the basal layer of the epidermis express the high affinity (trk E and trk) and the low affinity (p75) NGF receptors (NGF-R). NGF, known to be produced by keratinocytes, protects cells from death when it binds to NGF receptors. In cells, this NGF effect is mediated in part by induction of the protective protein Bcl-2. Interestingly, basal epidermal keratinocytes and melanocytes express Bcl-2 protein. Specifically, as described herein, it has now been demonstrated that melanocytes expressing the p75 NGF-R can be rescued from apoptotic cell death by the occupation of the p75 NGF-R with NGF or a substance capable of binding to the p75 NGF-R, which initiates the expression of the Bcl-2 protein.

Also as described herein, Applicants have now demonstrated that normal anagen hair follicles strongly express the p75 NGF-R and that p75 NGF-R expression is significantly reduced and limited to a few basal keratinocytes in telogen hair follicles.

As a result of these discoveries, methods are now available for inhibiting the process of apoptosis, or programmed cell death, in basal layer epidermal and follicular keratinocytes and melanocytes in vertebrates, specifically in humans. Thus, as a result of inhibition of apoptosis, the present invention relates to methods of inducing hair growth and coloration, and delaying hair loss and graying, as well as methods of inducing skin coloration in vertebrates. In addition, the present invention relates to methods of treating alopecia areata and baldness, as well as methods of preventing unwanted hair growth.

In one embodiment of the present invention, the invention relates to a method of preventing melanocyte loss after injury by inhibiting apoptosis in epidermal melanocytes. As described herein, Applicants have now demonstrated that p75 NGF-R mediated apoptosis is responsible for melanocyte loss after injury, for example, due to ultraviolet irradiation or aging. Specifically, Applicants have shown that an unoccupied p75 NGF-R (i.e., a p75 NGF-R which is not bound to ligand such as NGF) induces apoptotic cell death in melanocytes. Thus, ensuring that the p75 NGF-R is occupied by ligand inhibits the p75 NGF-R induced apoptotic pathway of cell death, resulting in the continued growth/proliferation, pigment production and pigment transfer to keratinocyte by epidermal melanocytes. Alternatively, epidermal melanocyte cell loss can be prevented by upregulating the expression of Bcl-2 protein in epidermal melanocytes, or by downregulating the expression of the p75 NGF-R in the melanocytes.

In another embodiment of the invention, the invention relates to a method of inducing hair growth in a vertebrate by upregulation of the expression of the p75 NGF-R on keratinocytes in a vertebrate, such as humans, by introducing into epidermal keratinocytes a nucleotide sequence encoding the p75 NGF-R. The p75 NGF-R gene product is expressed on the surface of the keratinocytes, and becomes available to bind to its naturally occurring ligand, NGF, or to another substance that mimics the binding activity of NGF (i.e., a pseudo-ligand). The p75 NGF-R binds its ligand, or pseudo-ligand, resulting in the expression of the protein, Bcl-2, which protects the keratinocyte from apoptosis.

Alternatively, the upregulation of the expression of the p75 NGF-R can be accomplished by introducing into the keratinocyte a substance, such as a transcription activator protein, which initiates the transcription of the p75 NGF-R gene.

Hair growth can also be induced or prolonged by the upregulation of the expression of the Bcl-2 protein in the keratinocytes, either by the introduction of a nucleotide sequence encoding the Bcl-2 protein or by the introduction of a substance that initiates transcription of the gene encoding the Bcl-2 protein.

In another embodiment of the present invention, the invention relates to a method of inducing hair color in a vertebrate, such as a human, by inhibiting p75 NGF-R mediated apoptosis of epidermal melanocytes. As described above, an unoccupied p75 NGF-R induces apoptosis in epidermal melanocytes. Ensuring that the p75 NGF-R is occupied by ligand, upregulating the expression of Bcl-2 protein, or downregulating the expression of p75 NGF-R inhibits apoptosis in epidermal melanocytes.

In another embodiment of the present invention, the invention relates to a method of inducing skin color in a vertebrate, particularly a human, by inhibiting p75 NGF-R mediated apoptosis of epidermal melanocytes. As described above, an unoccupied p75 NGF-R induces apoptosis in epidermal melanocytes. Ensuring that the p75 NGF-R is occupied by ligand, upregulating the expression of Bcl-2 protein, or downregulating the expression of p75 NGF-R inhibits apoptosis in epidermal melanocytes.

Conversely, apoptosis can be promoted in melanocytes and keratinocytes in humans, resulting in cell death. For example, cell death may be desirable to prevent unwanted hair growth (e.g., on women's faces or forearms). This can be accomplished, for example, by blocking nerve growth factor from binding to p75 NGF-R, thereby deceasing, or completely inhibiting production of Bcl-2 protein. Thus, apoptotic cell death would be promoted.

Another embodiment of the present invention relates to a method of identifying a substance capable of inhibiting apoptosis in melanocytes or keratinocytes by determining the effect the substance has on p75 nerve growth factor. Alternatively, the method of identifying a substance capable of inhibiting apoptosis in melanocytes or keratinocytes can be accomplished by determining the effect the substance has on Bcl-2 protein expression.

Thus, as a result of Applicants' discovery of the role of p75 NGF-R induced apoptosis in epidermal melanocytes, methods are now available to inhibit apoptotic cell death in epidermal and follicular melanocytes, as well as epidermal and follicular keratinocytes, including methods of inducing or prolonging hair growth, hair coloration and skin coloration.

BRIEF DESCRIPTION OF THE FIGURES

FIG. 1a is a photomicrograph depicting the effect of UV irradiation with 10 mJ/cm$^2$ on melanocytes.

FIG. 1b is a photomicrograph depicting the effect of sham irradiation on melanocytes.

FIG. 1c is a photomicrograph depicting the effect of UV irradiation with 10 mJ/cm$^2$ on MM4 cells.

FIG. 1d is a photomicrograph depicting the effect of sham irradiation on MM4 cells.

FIG. 1e is a photograph of an agarose gel stained with ethidium bromide depicting the effect of UV irradiation, of MM4 cells on DNA fragmentation.

FIG. 1f is a photomicrograph depicting the effect of UV irradiation of melanocytes on fragmentation of nuclear chromatin.

FIG. 1g is a photomicrograph depicting the effect of UV irradiation of melanocytes on homogenization of nuclear chromatin.

FIG. 1h is a bar graph depicting the percentage of propidium iodide-positive melanocytes after sham irradiation, UV irradiation with 10 mJ/cm$^2$ or UV irradiation with 25 mJ/cm$^2$.

FIG. 2a is bar graph depicting cell yields of melanocytes after 3 daily UV irradiations of 0, 5, 10 and 25 mJ/cm$^2$.

FIG. 2b is a bar graph depicting cell yields of MM4 after a single UV irradiation of 10 mJ/cm$^2$ and supplementation with 50 ng/ml NGF or diluent alone.

FIG. 2c is a bar graph depicting cell yields of MM4 after sham irradiation and supplementation with 50 ng/ml NGF or diluent alone.

FIG. 2d is a bar graph depicting cell yields of MM4 after a single UV irradiation of 10 mJ/cm$^2$ and supplementation with 50 ng/ml bFGF or diluent alone.

FIG. 2e is a bar graph depicting cell yields of MM4 after sham irradiation and supplementation with 50 ng/ml bFGF or diluent alone.

FIG. 2f is a photomicrograph depicting melanocyte cell morphology after UV irradiation daily for three days with 10 mJ/cm$^2$ and supplemented with diluent alone.

FIG. 2g is a photomicrograph depicting MM4 cell morphology after UV irradiation once with 10 mJ/cm$^2$ and supplemented with diluent alone.

FIG. 2h is a photomicrograph depicting melanocyte cell morphology after UV irradiation daily for three days with 10 mJ/cm$^2$ and supplemented with 50 ng/ml NGF.

FIG. 2i is a photomicrograph depicting MM4 cell morphology after UV irradiation once with 10 mJ/cm$^2$ and supplemented with 50 ng/ml NGF.

DETAILED DESCRIPTION OF THE INVENTION

Figure 3A:
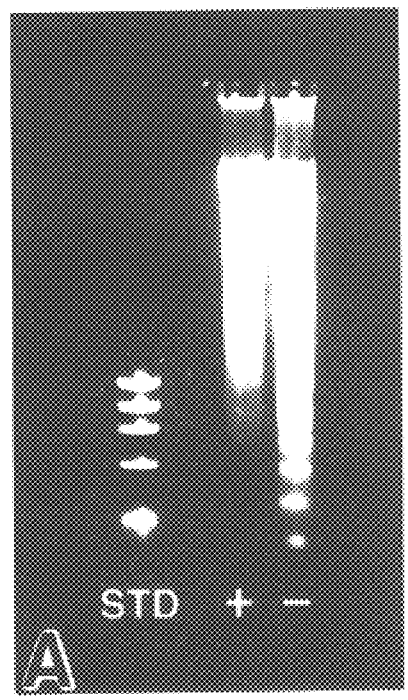
FIG. 3a is a photograph of an agarose gel stained with ethidium bromide depicting the effect of UV irradiation of MM4 cells supplemented with NGF on DNA fragmentation.

The present invention is based on Applicants' finding that basal layer melanocytes and keratinocytes undergo programmed cell death, or apoptosis. Specifically, Applicants have demonstrated that melanocytes and keratinocytes of the basal layer of the epidermis and the hair follicle undergo apoptosis. Apoptosis is an active process of self-destruction that occurs in vertebrate cells. Apoptosis follows a distinct pattern of events characterized by plasma membrane blebbing, cell volume contraction, nuclear pyknosis and inter nucleosomal DNA degradation following the activation of Ca+/Mg2+ dependent endonucleases. (Hockenberry, D. M., et al., *Cell* 75:241–251 (1993); Garcia, I., et al., *Science* 258:302–304 (1992)). Apoptosis is a highly conserved mechanism among species. Cells carry in their nuclei a genetic program for apoptosis, that can be activated upon the proper triggering, such as in response to changes in levels of hormones or growth factors in the cellular environment. (Allsopp, T. E., et al., *Cell* 295–307 (1993); Barinaga, M. et al., *Science* 259:762–763 (1992); Barinaga, M., et al., *Science* 263:754–755 (1994)). The "apoptotic" genes encode proteins which will induce apoptosis. However, recent evidence suggests that cells that do not undergo apoptosis express protective proteins, one of which is Bcl-2, which interact with the apoptotic proteins, sequester them and prevent their activity (Allsopp, T. E., et al., *Cell* 295–307 (1993)). It thus appears that a mechanism exists to protect cells from apoptosis.

To examine if UV-induced melanocyte death is apoptotic, cultures of pure human epidermal melanocytes or the human melanoma cell line MM4 (provided by Dr. U. Stierner, Goteborg, Sweden) were exposed to 5, 10 or 25 mJ/cm$^2$ UV irradiation, doses well within the physiologic UV range that reaches the basal layer of the epidermis during casual sun exposure. (See Example 1). Sham irradiated control cultures were handled identically but placed under a dark cloth adjacent to the UV beam. After 1–3 daily irradiations, many cells were detaching from the dish surface (See FIGS. 1a and 1c), while the majority of the cells in sham irradiated control cultures appeared healthy (See FIGS. 1b and 1d).

Total cellular DNA isolated from paired UV-irradiated cultures displayed the characteristic endonuclease-induced DNA fragmentation into multimers, the so-called DNA ladder, while DNA of sham irradiated controls was not fragmented (FIG. 1e). Duplicate UV-irradiated cultures stained with propidium iodide displayed the characteristic compaction. margination and fragmentation of nuclear chromatin, as well as homogenous nuclear staining (FIGS. 1f and 1g). In sham irradiated cultures, fewer than 6% of the cells stained positively with propidium iodide. In contrast, approximately 30% and 60% of cells irradiated with 10 and 25 mJ/cm$^2$ respectively were propidium iodide positive (FIG. 1h). These data strongly suggest that UV irradiation induces apoptotic death in cells of melanocytic origin.

However, melanocytes in vivo are not known to undergo apoptosis after UV-irradiation. As described herein, Applicants have demonstrated that these cells have a mechanism necessary to protect them from apoptotic cell death.

It had previously been shown that both the high affinity and low affinity nerve growth factor receptors, trk and p75 NGF-R, were expressed in vitro on the surface of appropriately stimulated human melanocytes. (Peacocke, M., et al., *Proc. Natl. Acad. Sci. U.S.A.* 85:5282–5286 (1988); Yaar, M., et al., *Clin. Res.* 40:531A (1992)). It had also been shown that keratinocytes express nerve growth factor. (Yaar, M., et al., *J. Cell Biol.* 115:821–828 (1991); DiMarco, E., et al., *J. Biol. Chem.* 266:21718–21722 (1991)).

Applicants now describe herein, that nerve growth factor-enhances the survival of human melanocytes after injury, for example, due to ultraviolet light exposure or growth factor deprivation.

Cultured human melanocytes were exposed to a solar simulator (5, 10, 25 mJ/cm$^2$ UVB dose) or sham irradiated as described in Example 1 and then maintained in suboptimal serum-free medium, and continuously provided with either 50 ng/ml nerve growth factor or diluent alone. (See Example 2). After UV irradiation, the majority of melanocytes and MM4 cells not supplemented with NGF were detaching from the dish surface. (See FIGS. 2f and 2g). In contrast, cultures supplemented with NGF appeared healthy. (See FIGS. 2h and 2i).

Cell yields of melanocytes (FIG. 2a) and MM4 cells (FIGS. 2b and 2c) irradiated with 10 mJ/cm$^2$ and supplemented with 50 ng/ml NGF were significantly higher than those of cells supplemented with diluent alone (melanocytes: 7 experiments p<0.0085; MM4 cells: 4 experiments p<0.0001, ANOVA). Furthermore, supplementation with basic fibroblast growth factor (bFGF), a major mitogen for cells of melanocytic origin (Halaban, R., et al., *In Vitro Cell Devel. Biol.* 23:47–52 (1987); Halaban, R., et al., *J. Cell Biol.* 107:1611–1619 (1988)), failed to improve MM4 cell survival after UV irradiation despite its mitogenic effect on sham irradiated cells (FIGS. 2d and 2e).

To explore the mechanism of the striking response of UV irradiated cells to NGF, paired cultures were irradiated with UVB light (5, 10 or 25 mJ/cm$^2$ UVB dose), or sham irradiated, and then incubated with antibodies to the high affinity component of the NGF receptor, trk. Melanocytes in UV-treated cultures displayed more trk receptors than sham irradiated controls. Northern blot analysis checking the mRNA levels of the p75 NGF-R showed several-fold higher transcript levels in NGF-supplemented melanocytes than in diluent controls.

To determine if melanocytes undergo p75 NGF-R mediated apoptotic cell death after UV irradiation, melanocytes were exposed to UVB (10 or 25 mJ/cm$^2$) or were sham irradiated, as described in Example 1, then maintained in suboptimal serum-free medium. Both UVB irradiation and suboptimal culture conditions, previously shown to induce p75 NGF-R expression on melanocytes, induced the DNA fragmentation patterns classic for apoptosis.

Figure 3B:
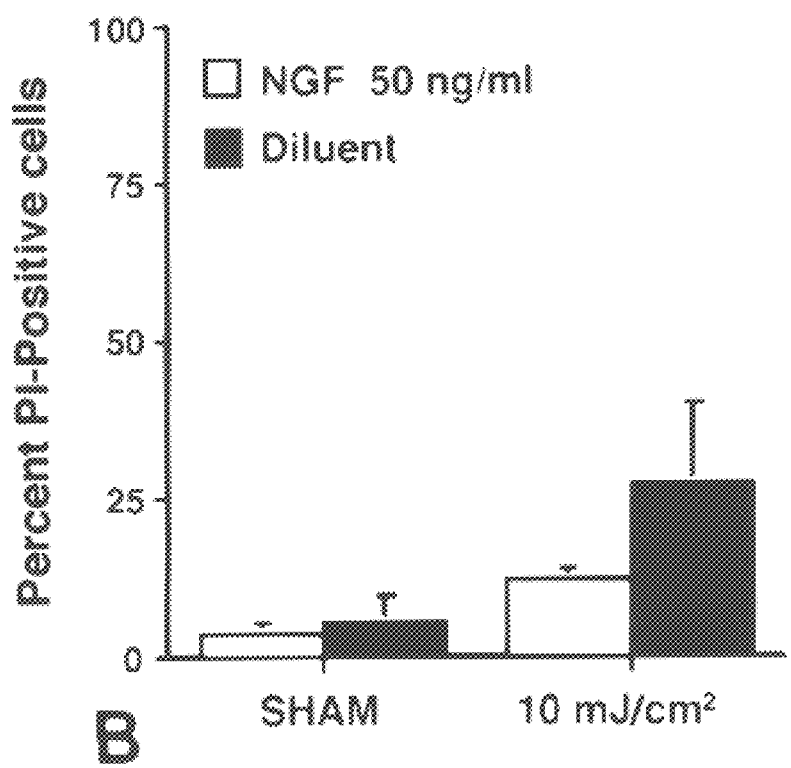
FIG. 3b is a bar graph depicting the percentage of propidium iodide-positive melanocytes after sham irradiation or UV irradiation with 10 mJ/cm and then treatment with 50 ng/ml NGF or diluent alone.

To determine whether NGF can rescue injured melanocytes from apoptosis, duplicate cultures were irradiated as described above, and maintained in medium containing 50 ng/ml NGF or diluent alone. Irradiated cultures not supplemented with NGF showed the characteristic DNA fragmentation, while cultures supplemented with NGF showed far less fragmentation (FIG. 3a). As described in Example 3, within twenty-four hours, in NGF-treated versus control melanocytes, 12% versus 30% of nuclei showed fragmentation (p less than 0.05, paired test). (FIG. 3b). Cell yields and thymidine labeling index determined daily for 19 days were higher in NGF-treated cultures (p less than 0.001), up to 6.5-fold and 10-fold, respectively.

To determine if melanocyte apoptosis is mediated by p75 NGF-R, cultures were treated as above, and then incubated in the presence of a blocking anti-human p75 NGF-R monoclonal antibody believed to act as a pseudo-ligand for the p75 NGF-R. (Anti-human p75 NGF-R monoclonal antibody courtesy of Moses V. Chao, Cornell University Medical Center, New York, N.Y.; Ross, et al., *Proc. Natl. Acad. Sci.* 81:6681 (1984)). Like NGF, the antibody suppressed melanocyte apoptosis in UV-irradiated cultures, while anti-rat p75 NGF-R antibody that did not bind the human p75 NGF-R had no effect.

Northern blot analysis of melanocyte RNA from donors of different ages showed that p75 NGF-R was higher in older donors, while in contrast the level for other growth factor receptors was unchanged or decreased with age, suggesting a greater vulnerability to apoptosis with aging, consistent with the clinical tendency for older persons to experience progressive hair loss.

Thus, one embodiment of the present invention relates to a method of preventing or inhibiting melanocyte cell loss after injury. The melanocytes are located in the basal epidermal layer and include melanocytes located in the skin and in hair follicles. The type of injury includes injury due to exposure to ultraviolet light, especially UVB, for example, in habitually sun-exposed skin, and injury due to the normal aging process. Injuries can also include disease conditions such as alopecia areata.

More specifically, the invention relates to methods of preventing, or inhibiting, apoptosis in melanocytes and keratinocytes. As described above, Applicants have shown that apoptosis in melanocytes is mediated by the p75 NGF receptor. If the receptor is occupied, that is, if the receptor has bound a ligand, apoptosis is inhibited in the cell.

The naturally-occurring ligand for the p75 NGF-R is nerve growth factor (NGF). Mammalian NGF is a protein, consisting of three subunits, α, β, and γ, which interact to form an approximately 130 kD complex. (Ulrich, A., et al., *Nature* 303:821–825 (1983)). However, all known effects of NGF are mediated by the 26 kD β-subunit through its receptor. There are two types of NGF receptors, one of a low molecular weight of approximately 75 kD, and the other of a higher molecular weight of approximately 140 kD. Both are believed necessary for the high affinity binding of NGF which is necessary for cellular response. The higher molecular weight receptor was recently found to be the protooncogene, trk, which is a member of the tyrosine kinase family. (Yaar, M., et al., *J. Cell Biol.*, 115:821–828 (1991); Chao, M., et al., *Science* 232:518–521 (1986); Klein, R. S., et al., *Cell* 65:189–197 (1991)). NGF has been sequenced and cloned as described in Ulrich, A., et al., *Nature*, 303:821–825 (1983), the teachings of which are herein incorporated by reference. Thus, the entire NGF protein complex, one of its active subunits, such as the 26 kD subunit, or any biologically active fragment of NGF can be used to occupy the receptor. The biological activity of an NGF protein fragment can be determined by in vitro bioassay, for example, as described in DiMarco, E., et al., *J. Biol. Chem.*, 266:21718–21722 (1991), the teachings of which are herein incorporated by reference.

Other substances that mimic NGF can act as a pseudo-ligand for the receptor. For example, the anti-human p75 NGF-R antibody described in Ross, et al., *Proc. Natl. Acad. Sci.* 81:6681 (1984) binds to p75 NGF-R and suppresses apoptosis in melanocytes. These substances include other neurotrophic factors and neurotrophins, such as NT-3, -4, and -5, which are also capable of binding to the p75 NGF-R. (DiMarco, E., et al., *J. Biol. Chem.*, 268:24290–24295 (1993); Yaar, M., et al., *J. Invest. Derm.*, 100:554 (1993)). Additional substances, either protein or chemical in nature, can be produced and evaluated for their NGF-R binding ability. For example, a chemical substance can be produced that mimics the composition of NGF. This substance can be evaluated as described above for NGF activity.

Alternatively, a method of preventing epidermal melanocyte cell loss can encompass downregulating the expression of the p75 NGF-R on epidermal melanocytes. This would also result in fewer unoccupied receptor molecules and hence, suppress apoptosis and prevent melanocyte cell loss. Downregulation can be accomplished, for example, by introducing into the melanocyte a substance that inhibits or decreases the transcription of the gene encoding the p75 NGF-R. For example, an antisense oligonucleotide which is complementary to the cellular mRNA encoding the p75 NGF-R can be introduced into the melanocyte in such a manner that the antisense oligonucleotide hybridizes with the mRNA, thereby preventing translation of the mRNA into p75 NGF-R protein.

Alternatively, epidermal melanocytes can be contacted with a substance which binds to p75 nerve growth factor receptor expressed on the surface of the melanocytes. The substance, for example, can be nerve growth factor in a pharmaceutically acceptable carrier or an antibody capable of binding to p75 nerve growth factor and acting as a psuedo-ligand. Pseudo-ligands include substances that mimic nerve growth factor, such as, e.g., peptides, organic molecules, antibodies and antibody fragments.

Psuedo-ligand antibodies which can be used in the present invention are capable of binding to p75 nerve growth factor receptor. The term antibody is intended to encompass both polyclonal and monoclonal antibodies. The preferred psuedo-ligand antibody is a monoclonal antibody reactive with a p75 nerve growth factor receptor. The term antibody is also intended to encompass mixtures of more than one antibody reactive with a p75 nerve growth factor receptor (e.g., a cocktail of different types of monoclonal antibodies reactive with a p75 nerve growth factor receptor). The term antibody is further intended to encompass whole antibodies, biologically functional fragments thereof, and chimeric antibodies comprising portions from more than one species, bifunctional antibodies, etc. Biologically functional antibody fragments which can be used are those fragments sufficient for binding of the antibody fragment to the p75 nerve growth factor receptor to occur.

The chimeric antibodies can comprise portions derived from two different species (e.g., human constant region and murine variable or binding region). The portions derived from two different species can be joined together chemically by conventional techniques or can be prepared as single contiguous proteins using genetic engineering techniques. The portions derived from two different species can also be produced by recombinant means and then joined as described above. DNA encoding the proteins of both the light chain and heavy chain portions of the chimeric antibody can be expressed as contiguous proteins or can be produced by recombinant means and joined using techniques known to those of skill in the art.

The end result of p75 NGF-R binding to its ligand is the expression of the protective protein, Bcl-2. Bcl-2 has been shown to prevent some classes of cell death in lymphocytes and neurons. (Veis, D. J., et al., *Cell* 75:229–240 (1993)). As described in Example 4, Applicants have now shown the expression of Bcl-2 by injured melanocytes after treatment with NGF. Apoptosis can be inhibited by the expression of the protective protein, Bcl-2. Thus, another method of preventing melanocyte cell loss comprises a method of upregulating expression of the Bcl-2 protein in melanocytes. This can be accomplished, for example, by inserting a nucleotide sequence encoding Bcl-2 into an expression vector capable of expressing the encoded Bcl-2 in vertebrate cells. Such an expression vector can be constructed, for example, as described in Allsopp, T. E., et al., *Cell* 73:295–307 (1993), the teachings of which are herein incorporated by reference. This Bcl-2 expression vector can then be introduced into melanocytes using standard laboratory techniques, such as, for example, microinjection, calcium-phosphate precipitation, or microprojectible bombardment.

Alopecia areata (AA) is a common disease of the hair follicle, affecting about 2% of new patients attending dermatology clinics in the United States and in Britain (Price, V. H., *J. Invest. Dermatol.*, 96:685 (1991)). In alopecia areata, the hair follicle, in response to some unknown signal or injury, is suddenly precipitated into premature telogen, and then cycles in a shortened aborted cycle in which it is repeatedly arrested part way through early anagen. The follicle may remain in this arrested state but is capable of resuming normal growth after months or years. The nature of the signal or injury and the anatomical target for this abnormality are unknown.

Histologically, AA is characterized by peribulbar lymphocytic infiltrate of predominantly T helper cells (Lever, W. F. and Schaumburg-Lever, G., eds., HISTOPATHOLOGY OF THE SKIN, J. B. Lippincott Co., Philadelphia, Pa., 1990, pp. 223–224), strongly suggesting the involvement of the cellular immune system perhaps through a loss of discrimination of self and non-self antigens (Goldsmith, L. A., *J. Invest. Dermatol.*, 96:985–1005 (1991)). Alternatively, an intrinsic abnormality in the follicular keratinocyte could be activated under the influence of internal or external triggers which eventually may lead to cellular degeneration and peribulbar inflammatory infiltrate. However, to date no specific antigen has been identified to support the autoimmune theory and no specific intrinsic difference has been reported between normal bulbar and AA keratinocytes.

Figure 5A:
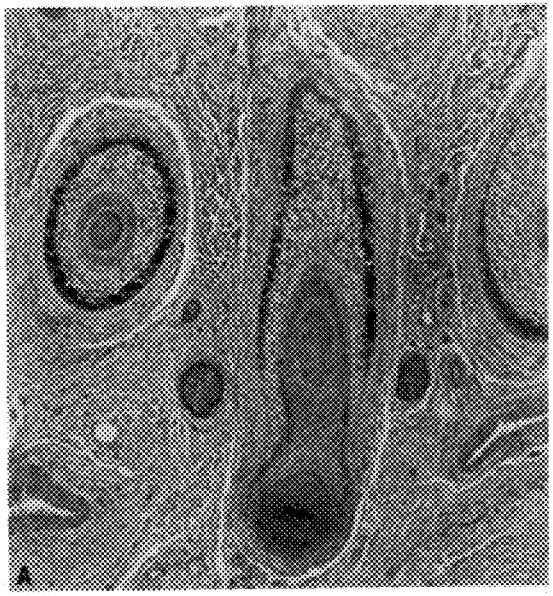
FIGS. 5a and 5b are photomicrographs showing the high levels of p75 NGF-R expression in melanocytes and bulbar keratinocytes of the outer root sheath in the lower portion of anagen hairs.
Figure 5B:
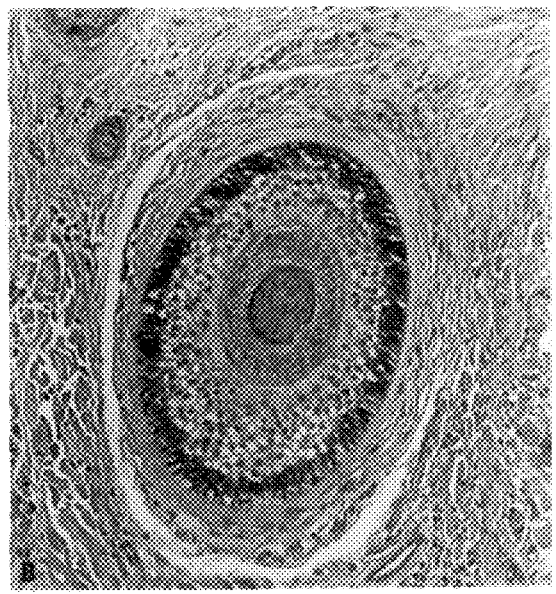
Figure 5C:
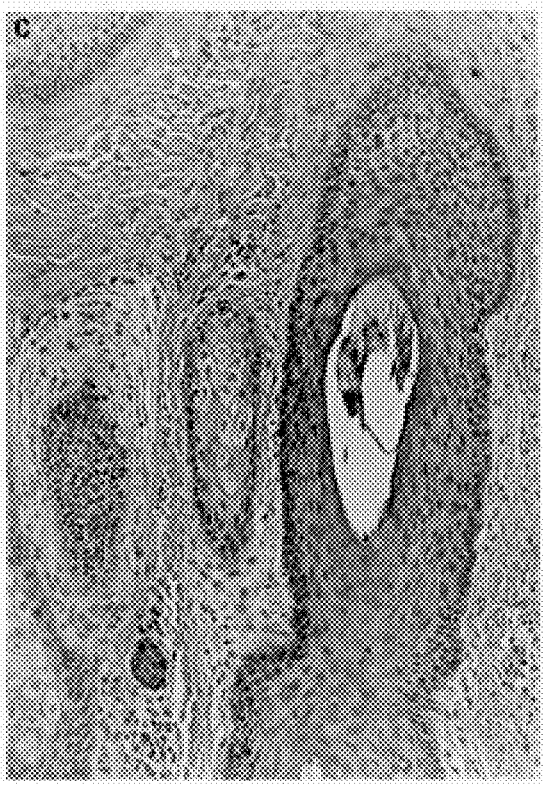
FIG. 5c is a photomicrograph showing p75 NGF-R levels in melanocytes and keratinocytes of telogen hairs.

As described in Example 5, indirect immunofluorescent studies were performed on biopsy material obtained from normal subjects and alopecia areata patients in an effort to detect differences in the NGF signalling system during conditions characterized by keratinocyte and melanocyte death. Results show high levels of p75 NGF-R in melanocytes and bulbar keratinocytes of the outer root sheath in the lower portion of anagen hairs (FIGS. 5a and 5b), suggesting a role for p75 NGF-R in hair growth. p75 NGF-R levels were significantly reduced or p75 NGF-R was absent melanocytes and keratinocytes of telogen hairs (FIG. 5c).

Furthermore, in melanocytes and keratinocytes in anagen hairs of AA patients, significantly lower levels of p75 NGF-R was also detected (FIGS. 5d and 5e), indicating that decreased levels of this receptor may be involved in the pathogenesis of AA by precipitating anagen hairs into early telogen.

These findings strongly suggest that loss of the p75 NGF-R may lead to bulbar keratinocyte apoptosis and shift the hair follicle towards telogen. Decreased p75 NGF-R in anagen hair of AA patients may be the initial insult which triggers telogen effluvium in these patients.

Thus, in another embodiment of the present invention, the invention relates to a method of inducing hair growth in a vertebrate. This is especially useful to delay or prevent hair loss in humans, for example, in male pattern baldness. Hair growth is induced by maintaining hairs in the anagen phase, and preventing the initiation of the telogen phase. As described above, p75 NGF-R levels were significantly reduced, or absent in alopecia areata patients. Thus, it is reasonable to believe that if the level of NGF-R expression on the surface of hair follicle keratinocytes is increased, the hairs are maintained in the anagen phase resulting in hair growth. Upregulating the expression of the p75 NGF-R can be accomplished by inserting a nucleotide sequence encoding the p75 NGF-R into an expression vector capable of expressing the encoded receptor protein in a vertebrate cell and introducing the receptor vector into the keratinocyte, resulting in expression of the encoded receptor. p75 NGF-R expression vectors can be constructed as described in, e.g., Rabizadeh, S., et al., *Science* 261:345–348 (1993); Morgenstern, J. P., et al., *Nucleic Acids Res.* 18:3587 (1990). This p75 NGF-R expression vector can be introduced into keratinocytes using standard laboratory techniques, such as, for example, microinjection, calcium-phosphate precipitation, or microprojectile bombardment. The cDNA sequences for human, rat and chicken p75 NGF-R are known. (Johnson, D., et al., *Cell* 47:545–554 (1986); Radeke, M. et al., *Nature* 325:593–597 (1987) and Large, T. H., et al., *Neuron* 2:1123–1134 (1989); Huer, J. G., et al., *Devl. Biol.* 137:287–304 (1990), respectively, the teachings of which are incorporated by reference).

Alternatively, a substance can be introduced into epidermal keratinocytes that upregulates the expression of the p75 NGF-R, such as a transcription factor that promotes the transcription of the gene encoding the p75 NGF-R.

As discussed above, unoccupied p75 NGF-R results in apoptosis in melanocytes. Based on the data presented herein, Applicants reasonably expect that p75 NGF-R/NGF mediated apoptosis also occurs in epidermal keratinocytes. Thus, the binding of p75 NGF-R to ligand in epidermal keratinocytes results in the expression of the anti-apoptotic protein, Bcl-2. Another method of inducing hair growth encompassed by the present invention relates to upregulating the expression of Bcl-2 in epidermal keratinocytes. Upregulation of Bcl-2 expression can be accomplished by expressing the encoded Bcl-2 protein in keratinocytes in a similar manner as the expression of Bcl-2 protein in melanocytes as discussed above.

As discussed above, in biopsies from patients with AA, p75 NGF-R expression in keratinocytes of anagen hairs is significantly reduced or totally absent. In AA, the p75 NGF-R can be bound in vivo by a pathogenic autoantibody that precludes further binding of commercial antibodies. To pursue the possibility that reduced levels of p75 NGF-R in AA are the result of a bound autoantibody, direct immunofluorescent studies can be performed on cross section from AA patients to determine if human immunoglobulins are bound in areas known to express p75 NGF-R.

Another embodiment of the present invention relates to methods of inducing hair coloration in a vertebrate comprising inhibiting apoptosis in epidermal melanocytes. Epidermal melanocytes produce melanin pigment in organelles called melanosomes and transfer the pigment to surrounding keratinocytes via extensive dendrites. Melanin pigmentation is the principal determinant of hair and skin color. Inhibiting apoptosis in melanocytes results in persistently pigmented keratinocytes, or hair coloration, and thus, delays or prevents hair greying which is due to loss of hair bulb melanocytes.

Conversely, as a result of Applicants'discovery of the mechanism of apoptotic cell death in melanocytes and keratinocytes, methods are also provided that promote, apoptosis in these cells resulting in cell death. The promotion of cell death in keratinocytes may be desirable to decrease, or completely inhibit hair growth in specific areas on an individual. For example, the inhibition of facial hair growth, forearm hair growth or leg hair growth is often desirable.

Such inhibition of hair growth can be accomplished, for example, by the use of a blocking antibody that will block the binding of NGF to the p75 NGF-R expressed on keratinocytes. The blocking antibody (or an antibody fragment or peptide) will bind to the p75 NGF-R and thus prevent NGF from binding to the NGF-R. Thus, the NGF/p75 NGF-R mediated anti-apoptotic pathway is inhibited and cell death will be permitted, or enhanced after injury to the cells. For example, the specific area in which hair growth is to be inhibited can first be irradiated with UV light and then a composition comprising the blocking antibody can be applied (e.g., in a cream or ointment), resulting in apoptosis of injured keratinocytes and inhibition of hair growth.

In another embodiment of the present invention, the invention relates to in vitro methods of identifying novel substances, capable of inducing hair growth or hair coloration or inhibiting hair growth in an individual. These methods can be based on Applicants'discovery of the apoptotic mechanism of death in melanocytes and keratinocytes. An in vitro method of evaluating p75 NGF-R/NGF mediated apoptosis can use, for example, C57BL-6 mouse skin specimens with synchronized hair follicles either in telogen or anagen, as described in Paus, R., et al., *Br. J. Dermatol.* 122:777–784 (1990), the teachings of which are incorporated herein by reference. These skin specimens, being larger than biopsies obtained from people, and having follicles in defined portions of the growth cycle are useful to investigate the relationship between NGF/NGF-R and growth state of the hair follicle. The necessary murine probes (cDNA and antibodies) are available. For example, anti-rat p75 NGF-R antibody is available from Accurate Chemical & Scientific Company (New York) and anti-mouse NGF antibody is available from Boehringer Mannheim Biochemicals (Indianapolis, Ind.). Rat NGF cDNA is described in Maisonpierre, P. C., et al., *Science* 247:1446–1451 (1990) and rat p75 NGF-R cDNA is described in Radeke, M. J. et al., *Nature* 325:593–597 (1987). A substance to be tested for anti-apoptotic activity in melanocytes can be evaluated in this, or another a melanocyte cell culture assay (e.g., as described in Example 1). Skin specimens or melanocytes can be maintained under conditions suitable for their proliferation and then exposed to UV irradiation. After irradiation, the substance to be tested for apoptotic activity can be added to the culture system. Subsequently, the cultured cells can be evaluated to determine whether cell death has been inhibited, or decreased.

Substances identified in this method are substances that specifically alter the apoptotic mechanism in melanocytes and kerantincytes. For example, substances that mimic nerve growth factor can be tested in an assay such as described above to evaluate their activity in inhibiting apoptosis. Additionally, substances identified and evaluated by this method can be peptides, organic molecules, small organic molecules, antibodies or antibody fragments.

Substances identified using methods described herein, found to bind p75 nerve growth factor receptor, or otherwise affect p75 nerve growth factor receptor, or found to initiate Bcl-2 expression, can be used in methods to induce hair growth, hair color or skin color. These methods comprise contacting epidermal cells, including basal layer melanocytes or follicular keratinocytes, of a vertebrate with an effective amount of a substance capable of inducing hair growth, hair color or skin color by inhibiting apoptosis in melanocytes or keratinocytes. An effective amount of such an identified substance is an amount effective to significantly decrease or completely inhibit apoptotic cell death in melanocytes and keratinocytes. The decrease of inhibition of apoptosis in melanocytes and keratinocytes can be evaluated using the methods described herein.

Various delivery systems are known and can be used to administer effective amounts of substances, such as naturally-occurring ligands or pseudo-ligands for p75 nerve growth factor receptor to inhibit apoptosis in melanocytes and keratinocytes. For example, encapsulation in liposomes, microparticles, microcapsules, expression by recombinant cells, receptor-mediated endocytosis, construction of a naturally-occurring or pseudo-ligand encoding nucleic acid as part of a retroviral or other vector can be used. In one embodiment, a liposome preparation can be used. The liposome preparation can be comprised of any liposomes which penetrate the stratum corneum and fuse with the cell membrane, resulting in delivery of the contents of the liposome into the cell. For example, liposomes such as those described in U.S. Pat. No. 5,077,211 of Yarosh, U.S. Pat. No. 4,621,023 of Redziniak et al. can be used.

Administration of the substances can also be, for example, by topical application to the epidermis of a vertebrate, such as a human, in a quantity sufficient to suppress apoptosis and prevent melanocyte or keratinocyte cell loss. The substance can be admixed in a pharmacological topical carrier such as a gel, an ointment, a lotion, a cream, or a shampoo and will include such carriers as water, glycerol, alcohol, propylene glycol, fatty alcohols, triglycerides, fatty acid esters, or mineral oils. Other possible topical carriers include, e.g., liquid petrolatum, isopropyl palmitate, polyethylene glycol, ethanol (95%), polyoxyethylene monolauriate (5%) in water, sodium lauryl sulfate (5%) in water. Other materials such as anti-oxidants, humectants, viscosity stabilizers, and similar agents may be added as necessary.

In addition, in certain instances, it is expected that the substances can be disposed within devices placed upon, in, or under the skin. Such devices include transdermal patches, implants, and injections which release the substance in such a manner as to contact the skin or hair follicle either by passive or active release mechanisms.

The delivery vehicle can also contain perfumes, colorants, stabilizers, sunscreens, or other ingredients. The substance can be applied, for example, topically to the epidermis at regular intervals, such as once or twice daily, in a suitable vehicle and at an effective concentration. Application can also be in a vehicle which specifically targets the appropriate cells (i.e., either epidermal melanocytes or epidermal keratinocytes). For example, a membrane marker specific for melanocytes, such as melanocyte stimulating hormone (MSH), can be incorporated into a liposome containing a substance that inhibits or decreases the transcription of the gene encoding the p75 NGF-R.

An effective amount of a substance that inhibits, decreases, or promotes apoptosis can be administered to an individual using any of the above-described methods. The actual preferred amounts of a ligand to be administered will vary according to the specific ligand being utilized, the particular compositions formulated, the mode of application, and the particular situs and vertebrate being treated. The concentration of the ligand effective to suppress apoptosis and to prevent epidermal melanocyte cell loss or epidermal keratinocyte cell loss, or to promote apoptosis, in a vertebrate, such as a human, can be determined using known, conventional pharmacological protocols.

The following examples more specifically illustrate the invention and are not intended to be limiting in any way.

EXAMPLE 1

Effect of UV Irradiation on Melanocytic Cell Death

Melanocytes or MM4 cells were plated in 60 mm diameter tissue culture dishes. Melanocytes were maintained in Medium 199 supplemented with 7% fetal bovine serum (FBS), 10 ng/ml epidermal growth factor (Collaborative Research), 10 $\mu$g/ml insulin (Sigma), $10^{-9}$ M triiodothyronine (Collaborative Research), 10 $\mu$g/ml transferrin (Sigma), $1.4 \times 10^{-6}$ M hydrocortisone (Calbiochem), $10^{-9}$ M cholera toxin (Calbiochem), and 10 ng/ml basic fibroblast growth factor (Collaborative Research) (basal melanocyte medium). MM4 cells were maintained in 55.3% DME, 27.6% L15, 15% FBS, 1% nonessential amino acids (GIBCO BRL), 2 mM glutamine and 10 $\mu$g/ml insulin. After 24 hours, medium was replaced by phosphate buffered saline (PBS) and cells were irradiated using a 1 KW xenon arc solar simulator (XMN 1000-21, Optical Radiation Corp., Azuza, Calif.) with 5, 10, or 25 mJ/cm² UV through the petri dish plastic cover. Irradiance was adjusted to $4 \times 10^{-5}$ UV cm$^{-2}$ and metered with a research radiometer (model IL1700A, International Light, Newburyport, Mass.) fitted with a UVB probe at 285±5 nm. After UV irradiation, cells were maintained in their respective media without FBS for 2 days (MM4 cells) or 3 days (melanocytes) and processed as indicated. Sham irradiated control cultures were handled identically but placed under a dark cloth adjacent to the UV beam.

Cells in 100 mm tissue culture dishes were washed with cold PBS and disrupted in lysis buffer pH8 (10 mM tris, 150 mM NaCl, 0.1 mM EDTA, 1% SDS, 200 $\mu$g/ml proteinase K). After 15 hour incubation at 37° C., samples were extracted twice with phenol plus chloroform (1:1, V/V) and precipitated overnight with ethanol (2.5×volume) and 3 M sodium acetate (1/10×volume). The DNA was then digested with DNAse free ribonuclease (10 $\mu$g/ml) for one hour at 37° C., separated on 1% agarose gel and stained with ethidium bromide. The size marker is 100 bp DNA ladder (STD) (Gibco/BRL, Gaithersburg, Md.). FIG. 1e shows that DNA fragmentation occurs in UV-irradiated but not sham irradiated MM4 cells.

Melanocytes were cultured on 8 chamber tissue culture slides (Nunc Inc., Naperville, Ill.) and were UV irradiated with 10 mJ/cm² as above. Four $\mu$M of propidium iodide (PI) was added to melanocyte cultures 24 hours after irradiation, for 5 minutes at 37° C. Cultures were washed with PBS and nuclei were analyzed using a Leitz confocal laser microscope (Leica, Deerfield, Ill.). FIG. 1f shows fragmentation of nuclear chromatin of UV-irradiated melanocytes. FIG. 1g shows homogenization of nuclear chromatin of UV-irradiated melanocytes.

Melanocytes were sham or UV irradiated with 10 mJ/cm² and 25 mJ/cm². Twenty-four hours after irradiation, 4 $\mu$M of propidium iodide was added to cultures as above and cells were viewed with fluorescent phase contrast Nikon microscope. The number of fragmented or homogeneously stained nuclei versus nonstained nuclei was determined in several representative fields and expressed as a percent of total cells. A minimum of 130 cells were counted for each condition. FIG. 1h shows the percent PI-positive cells in melanocyte culture.

EXAMPLE 2

Nerve Growth Factor Enhances Survival of Human Melanocytes After Injury

Melanocytes were UV-irradiated three times on three consecutive days with 0, 5, 10 or 25 mJ/cm² doses. After each UV exposure, cells were placed until the next irradiation in fresh melanocyte medium containing 50 ng/ml NGF or diluent alone. FIG. 2a shows melanocyte yield after three daily UV irradiations of 0, 5, 10 and 25 mJ/cm².

FIGS. 2b and 2d show MM4 cell yields 24–72 hours after a single UV irradiation of 10 mJ/cm². FIGS. 2c and 2e show MM4 cell yields 24–72 hours after sham irradiation. Cells in FIGS. 2b and 2c were supplemented with 50 ng/ml NGF or diluent alone. Cells in FIGS. 2d and 2e were supplemented with 50 ng/ml bFGF or diluent alone.

FIG. 2f shows the cell morphology of melanocytes after UV irradiation daily for three days with 10 mJ/cm² and supplemented with diluent alone. FIG. 2g shows the cell morphology of MM4 cells after UV irradiation once with 10 mJ/cm² and supplemented with diluent alone. FIG. 2h shows the cell morphology of melanocytes after UV irradiation daily for three days with 10 mJ/cm and supplemented with 50 ng/ml NGF. FIG. 2i shows the cell morphology of MM4 cells after UV irradiation once with 10 mJ/cm² and supplemented with 50 ng/ml NGF.

EXAMPLE 3

Nerve Growth Factor Rescues Injured Melanocytes Undergoing Apoptosis

Melanocytes or MM4 cells were plated as described in Example 1. After irradiation, melanocytes were maintained in basal melanocyte medium lacking FBS and hydrocortisone, with 50 ng/ml NGF or diluent alone (melanocyte medium). MM4 cells were maintained in DME supplemented with 50 ng/ml NGF or diluent alone.

Twenty-four hours after UV irradiation, cells supplemented with diluent alone (−) showed fragmentation, while DNA of cells supplemented with NGF (+) was not fragmented. The standard (STD) is 100 bp DNA ladder (Gibco/BRL). (See FIG. 3a).

Melanocytes were irradiated with 10 mJ/cm² or were sham irradiated as in Example 1 and then provided 50 ng/ml NGF or diluent alone. Twenty-four hours after irradiation, approximately 30% of diluent treated cells but only 12%, of NGF supplemented cultures show positive nuclei. That is, propidium iodide staining was positive in approximately 30% of nuclei in cultures not supplemented with NGF but in only 12% positive nuclei in NGF-supplemented cultures. (See FIG. 3b).

EXAMPLE 4

Melanocyte Expression of Bcl-2 Protein After UV Injury

To determine if NGF induces Bcl-2 protein, MM4 cells were UV-irradiated with 10 mJ/cm$^2$ or sham irradiated and then supplemented with NGF or diluent alone as explained in Example 3. Twenty-four hours after irradiation, cells were washed-with PBS and then detached with 0.5 mM EDTA and washed again with PBS. 10$^6$ cells were incubated with 3.25 µg/ml mouse anti human Bcl-2 monoclonal antibody (DAKO Co., Carpinteria, Calif.) or with the same concentration of normal mouse IgG (Cappel, Organon Teknika Co., West Chester, Pa. U.S.A.) in PBS with 0.3% Saponin (Sigma, St, Louis, Mo.) for 2 hours at 4° C. After three washes with PBS, cells were incubated with fluorescein-conjugated goat anti-mouse IgG (1 hour at 4° C.) (Cappel), washed four times in PBS, fixed with 0.1% fresh formaldehyde, and washed three times in PBS. Fluorescence intensity was determined using FACScan flow cytometer (Becton-Dickinson, San Jose, Calif.).

Figure 4A:
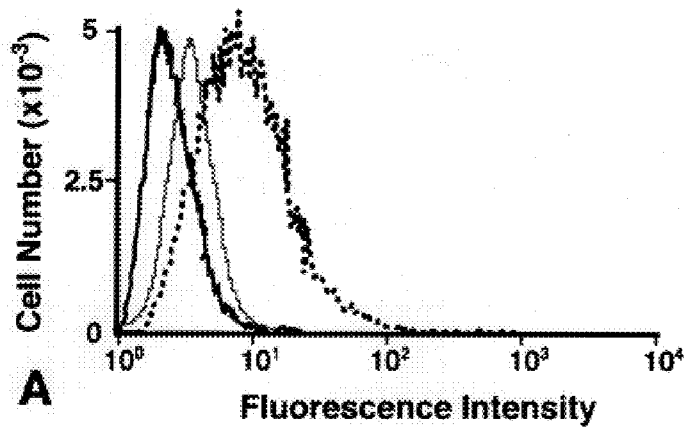
FIG. 4a is a graphic representation depicting the effect of NGF on Bcl-2 expression in MM4 cells UV-irradiated with 10 mJ/cm$^2$.
Figure 4B:
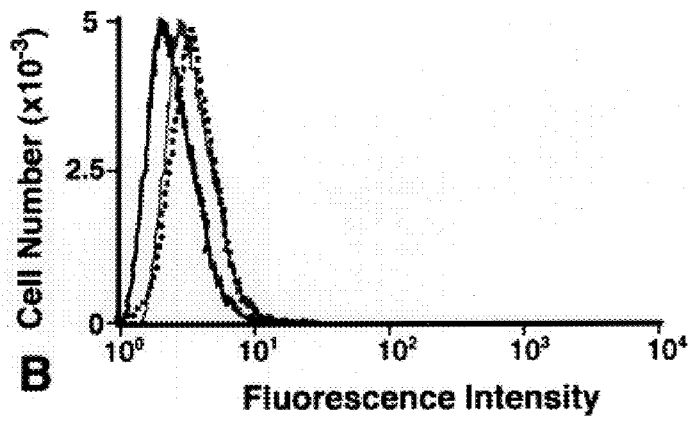
FIG. 4b is a graphic representation depicting the effect of NGF on Bcl-2 expression in MM4 cells sham irradiated.

The results show that UV-irradiated (FIG. 4a) or sham irradiated (FIG. 4b) cells, cells supplemented with diluent alone, or sham irradiated cells supplemented with NGF had only low levels of Bcl-2 protein FACScan analysis. However, the Bcl-2 level was substantially higher in cells subjected to UV irradiation followed by NGF supplementation (FIG. 4a). (–) mouse IgG control; ( . . . ) diluent alone; ( . . . ) 50 ng/ml NGF.

Figure 4C:
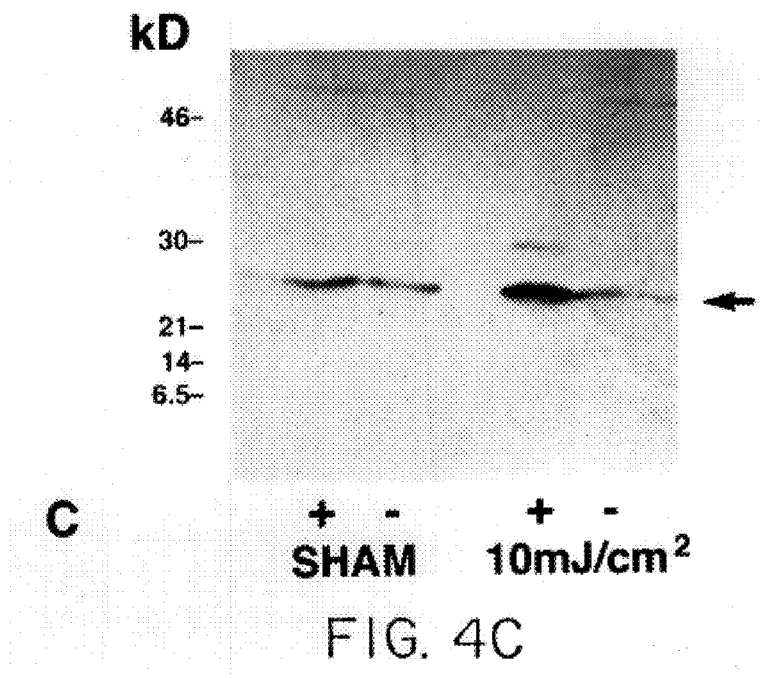
FIG. 4c is a photograph of a Western blot depicting the effect of NGF on Bcl-2 expression in MM4 cells UV-irradiated or sham irradiated.

Proteins from duplicate cultures analyzed by Western blotting confirmed Bcl-2 induction in UV irradiated NGF supplemented melanocytic cells (FIG. 4c). MM4 cells were extracted in RIPA buffer (50 mM Tris-HCl [pH 8.0], 0.15 M NaCl, 0.5% sodium deoxycholate, 1% Triton X-100) in the presence of one µg/ml aprotinin and 75 µg/ml phenylmethylsulfonyl fluoride, sonicated for 1–3 seconds and centrifuged. 45 µg of protein per lane were separated on 12% SDS/PAGE and blotted onto nitrocellulose paper (overnight, 40V). Blots incubated with 3.25 µg/ml anti-human Bcl-2 antibody (DAKO) reveal a band at the reported 25 kDa molecular weight: (+) 50 ng/ml NGF, (–) diluent alone.

EXAMPLE 5

Immunofluorescent Studies

Punch biopsies (6 mm diameter) can be obtained from scalps of patients for example, with patchy AA, alopecia totalis, alopecia universalis as well as uninvolved sites of AA patients and age matched controls and snap frozen for immunofluorescent studies. Immunostaining of fresh frozen tissues is compared with formaldehyde fixed tissues to determine if the antigen detection level is better in frozen sections. If the antibodies recognize formaldehyde fixed antigens with the same accuracy as non-denatured antigen, formaldehyde fixed tissues can be used for the immunofluorescent studies.

Figure 5D:
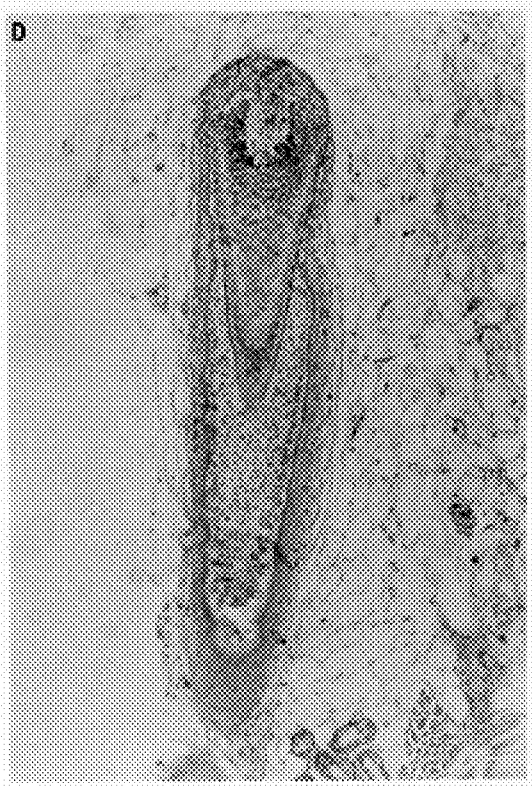
FIGS. 5d and 5e are photomicrographs showing p75 NGF-R levels in melanocytes and keratinocytes in anagen hairs of patients with alopecia areata.
Figure 5E:

Immunofluorescence was performed as described in Yaar, M., et al., *Lab Invest*. 58:157 162 (1988). Briefly, 4–µM thick vertical sections of biopsy samples were incubated with the first antibody overnight at 4° C. The second antibody applied was the appropriate fluorescein isothiocyanate conjugated antibody: either goat anti-rabbit or anti-mouse IgG (Cooper Biomedical). The second antibody was incubated for 30 minutes. Quantitation was performed by analysis of fluorescence intensity on the Leica Confocal microscope as described in Lu, K., et al., *Proc. Natl. Acad. Sci. USA* 89:3889–3893 (1992). FIGS. 5a and 5b show high levels of p75 NGF-R in melanocytes and bulbar keratinocytes of the outer root sheath in the lower portion of anagen hairs. FIG. 5c shows that p75 NGF-R levels were significantly reduced or absent melanocytes and keratinocytes of telogen hairs. FIGS. 5d and 5e show that p75 NGF-R levels were significantly lower or absent in melanocytes and keratinocytes in anagen hairs of AA patients.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting human epidermal melanocyte cell loss comprising inhibiting p75 nerve growth factor receptor-mediated apoptosis in the melanocyte by contacting said melanocytes with an isolated ligand, in an amount sufficient to inhibit cell loss, wherein the ligand comprises:

a) a neurotrophin selected from the group consisting of: nerve growth factor, the 26 kD β-subunit of nerve growth factor, neurotrophin-3 and neurotrophin-4/5; or b) a biologically active fragment of a neurotrophin selected from the group consisting of: nerve growth factor, the 26 kD β-subunit of nerve growth factor, neurotrophin-3 and neurotrophin-4/5;

wherein said ligand binds p75 nerve growth factor receptor, thereby inhibiting apoptosis and preventing cell loss.

2. A method of maintaining hair growth in a human comprising inhibiting p75 nerve growth factor receptor-mediacted apoptosis in keratinocytes by contacting said keratinocytes with an isolated ligand in an amount sufficient to inhibit cell loss, wherein the ligand comprises:

a) a neurotrophin selected from the group consisting of: nerve growth factor, the 26 kD β-subunit of nerve growth factor, neurotrophin-3 and neurotrophin-4/5; or b) a biologically active fragment of a neurotrophin selected from the group consisting of: nerve growth factor, the 26 kD β-subunit of nerve growth factor, neurotrophin-3 and neurotrophin-4/5;

wherein said ligand binds p75 nerve growth receptor, thereby inhibiting apoptosis, and maintaining hair growth.

3. A method of treating alopecia areata in a human comprising inhibiting p75 nerve growth factor receptor-mediated apoptosis in keratinocytes by contacting the keratinocyte with an isolated ligand, in an amount sufficient to inhibit apoptosis, wherein the ligand comprises:

a neurotrophin selected from the group consisting of: nerve growth factor, the 26 kD β-subunit of nerve growth factor, neurotrophin-3 and neurotrophin-4/5; or b) a biologically active fragment of a neurotrophin selected from the group consisting of: nerve growth factor, the 26 kD β-subunit of nerve growth factor, neurotrophin-3 and neurotrophin-4/5;

wherein said ligand binds p75 nerve growth receptor, thereby inhibiting apoptosis, and maintaining hair growth.

4. A method of treating male patter baldness in a human comprising maintaining hair growth in the male comprising inhibiting p75 nerve growth factor receptor-mediated apoptosis in keratinocytes by contacting the keratinocyte with an isolated ligand, in an amount sufficient to inhibit apoptosis, wherein the ligand comprises:

a) a neurotrophin selected from the group consisting of: nerve grow factor, the 26 kD β-subunit of nerve growth factor, neurotrophin-3 and neurotrophin-4/5; or b) a biologically active fragment of a neurotrophin selected from the group consisting of: nerve growth factor, the 26 kD β-subunit of nerve growth factor, neurotrophin-3 and neurotrophin-4/5;

wherein said ligand binds p75 nerve growth receptor, thereby inhibiting apoptosis, and maintaining hair growth.

5. The method of claim 1 wherein the ligand is in a pharmaceutically acceptable carrier.

6. The method of claim 1 wherein the ligand is topically applied.

7. The method of claim 2 wherein the ligand is topically applied.

8. The method of claim 3 wherein the ligand is topically applied.

9. The method of claim 4 wherein the ligand is topically applied.

10. The method of claim 2 wherein the ligand is in a pharmaceutically acceptable carrier.

11. The method of claim 3 wherein the ligand is in a pharmaceutically acceptable carrier.

12. The method of claim 1, wherein the ligand is at a concentration of less than 1.5 μM.

13. A method of maintaining hair color in a human comprising inhibiting p75 nerve growth factor receptor-mediated apoptosis in human melanocytes by contacting the melanocyte with an isolated ligand, in an amount sufficient to inhibit apoptosis, wherein the ligand comprises:

a) a neurotrophin selected from the group consisting of: nerve growth factor, the 26 kD β-subunit of nerve growth factor, neurotrophin-3 and neurotrophin-4/5; or b) a biologically active fragment of a neurotrophin selected from the group consisting of: nerve growth factor, the 26 kD β-subunit of nerve growth factor, neurotrophin-3 and neurotrophin-4/5;

wherein said ligand binds p75 nerve growth factor, receptor, thereby inhibiting apoptosis and maintaining hair color.

14. The method of claim 13, wherein the ligand is topically applied.

15. The method of claim 13, wherein the ligand is at a concentration less than 1.5 μM.

16. A method of maintaining skin color in a human comprising inhibiting p75 nerve growth factor receptor-mediated apoptosis in human melanocytes by contacting the melanocyte with an isolated ligand, in an amount sufficient to inhibit apoptosis, wherein the ligand comprises:

a) a neurotrophin selected from the group consisting of: nerve growth factor, the 26 kD β-subunit of nerve growth factor, neurotrophin-3 and neurotrophin-4/5; or b) a biologically active fragment of neurotrophin selected from the group consisting of: nerve growth factor, the 26 kD β-subunit of nerve growth factor, neurotrophin-3 and neurotrophin-4/5;

wherein said ligand binds p75 nerve growth factor receptor, thereby inhibiting apoptosis and maintaining skin color.

17. The method of claim 16, wherein the ligand is topically applied.

18. The method of claim 16, wherein the ligand is at a concentration of less than 1.5 βM.

19. A method of inhibiting human epidermal keratinocyte cell loss comprising inhibiting p75 nerve growth factor receptor-mediated apoptosis in the keratinocyte by contacting the human keratinocyte with an isolated ligand, in an amount sufficient to inhibit cell loss, wherein the ligand comprises:

a) a neurotrophin selected from the group consisting of: nerve growth factor, the 26 kD β-subunit of nerve growth factor, neurotrophin-3 and neurotrophin-4/5; or b) a biologically active fragment of a neurotrophin selected from the group consisting of: nerve growth factor, the 26 kD β-subunit of nerve growth factor, neurotrophin-3 and neurotrophin-4/5;

wherein said ligand binds p75 nerve growth receptor, thereby inhibiting epidermal keratinocyte cell loss.

20. The method of claim 19, wherein the ligand is topically applied.

21. The method of claim 19, wherein the ligand is at a concentration of less than 1.5 βM.

22. The method of claim 2, wherein the ligand is at a concentration of less than 1.5 βM.

23. The method of claim 3, wherein the ligand is at a concentration of less than 1.5 βM.

24. The method of claim 4, wherein the ligand is in a pharmaceutically acceptable carrier.

25. The method of claim 4, wherein the ligand is at a concentration of less than 1.5 βM.

26. The method of claim 13, wherein the ligand is in a pharmaceutically acceptable carrier.

27. The method of claim 16, wherein the ligand is in a pharmaceutically acceptable carrier.

28. The method of claim 19, wherein the ligand is in a pharmaceutically acceptable carrier.

* * * * *

UNITED STATES PATENT AND TRADEMARK OFFICE
CERTIFICATE OF CORRECTION

PATENT NO. : 6,103,689
DATED : August 15, 2000
INVENTOR(S) : Barbara A. Gilchrest, Mina Yaar and Mark Eller It is certified that error appears in the above-identified patent and that said Letters Patent is hereby corrected as shown below:

Column 16,
Line 59, delete "patter" and insert -- pattern --;

Column 18,
Lines 11, 31, 33, 35 and 40, delete "1.5βM" and insert -- 1.5 μM--.

Signed and Sealed this

Thirty-first Day of August, 2004

JON W. DUDAS
*Director of the United States Patent and Trademark Office*